(12) United States Patent
Ross, III et al.

(10) Patent No.: US 7,144,111 B1
(45) Date of Patent: Dec. 5, 2006

(54) OPHTHALMOSCOPY LENS SYSTEM

(76) Inventors: Denwood F. Ross, III, 8420 Center Rd. South, Austinburg, OH (US) 44010; Larry Jones, 13571 Ashford Wood Ct. West, Jacksonville, FL (US) 32218

( * ) Notice: Subject to any disclaimer, the term of this patent is extended or adjusted under 35 U.S.C. 154(b) by 404 days.

(21) Appl. No.: 10/689,567

(22) Filed: Oct. 20, 2003

Related U.S. Application Data

(60) Provisional application No. 60/419,447, filed on Oct. 18, 2002.

(51) Int. Cl.
*A61B 3/125* (2006.01)
(52) U.S. Cl. .................. 351/219; 351/205; 351/206; 606/4
(58) Field of Classification Search ........... 351/200, 351/205, 206, 219, 221, 246; 606/4
See application file for complete search history.

(56) References Cited

U.S. PATENT DOCUMENTS 5,200,773 A * 4/1993 Volk ........................ 351/219
5,523,810 A * 6/1996 Volk ........................ 351/219
5,526,074 A * 6/1996 Volk ........................ 351/219
6,019,472 A * 2/2000 Koester et al. ............ 351/219
6,164,779 A * 12/2000 Volk ........................ 351/219

* cited by examiner

*Primary Examiner*—Charles A. Marmor, II
*Assistant Examiner*—John R Sanders
(74) *Attorney, Agent, or Firm*—Dinsmore & Shohl, LLP

(57) ABSTRACT

A gonioscopic lens system which provides a real image of the anterior chamber angle of a patient's eye. The lens system includes a first lens group having a concave posterior surface configured to be placed on a patient's eye, a second lens group optically aligned with the first lens group; and a stop positioned between the first and second lens groups. An achromatic gonioscopic lens system which provides a real image of the anterior chamber angle of a patient's eye is also provided, as well as an ophthalmoscopy lens system for viewing both the anterior chamber angle and the retina of a patient's eye.

16 Claims, 2 Drawing Sheets

OPHTHALMOSCOPY LENS SYSTEM

This application claims the benefit of U.S. Provisional Application Ser. No. 60/419,447 filed on Oct. 18, 2002, the entire disclosure of which is hereby incorporated herein by reference.

BACKGROUND OF THE INVENTION

1. Field of the Invention

The present invention relates to ophthalmoscopy lens systems, particularly those employed with a slit lamp or other biomicroscope for the diagnosis and/or treatment of the eye.

2. Description of Related Art

During the diagnosis and treatment of the eye, it is typically necessary to provide a means for viewing various structures within the eye. Various ophthalmoscopy lens systems have been developed for this purpose. By way of example, "indirect" ophthalmoscopy lens systems have been developed. Such lens systems produce an aerial image of structures within the patient's eye, and such real images may be viewed using, for example, a slit lamp biomicroscope or other indirect ophthalmoscope. Direct ophthalmoscopy lens systems, on the other hand, produce a virtual image within the eye of structures within the patient's eye, such as the fundus (including the retina). The virtual image produced by direct ophthalmoscopy lens systems can be readily viewed by the practitioner. In general, direct ophthalmoscopic lens systems can provide greater magnification than indirect ophthalmoscopy lens systems, however, direct lens systems generally provide a smaller field of view.

The field of view provided by an ophthalmoscopy lens system can be significant in the diagnosis and treatment of certain eye conditions. In particular, special "gonioscopic" lens systems have been developed for viewing the anterior chamber angle of a patient's eye. The "anterior chamber angle" refers to the geometric angle where the iris and cornea meet. Fluid within the eye drains through the anterior chamber angle into channels which provide drainage. If the anterior chamber angle is narrowed, fluid flow may be obstructed resulting in an increase in pressure within the eye. Such an increase in pressure is often associated with glaucoma. Therefore, the diagnosis and treatment of glaucoma typically requires that the practitioner examine the anterior chamber angle. Observation of the anterior chamber angle, however, generally requires a lens systems which provides an extremely wide field of view.

Most gonioscopic lenses used to examine the anterior chamber angle rely on mirrors in order to achieve the required field of view (such as a "Goldmann" lens). Alternatively, U.S. Pat. No. 6,164,779, which is incorporated herein by way of reference, discloses various gonioscopic lens systems, many embodiments of which do not rely upon reflective surfaces for providing the desired field of view.

SUMMARY OF THE INVENTION

The present invention provides a gonioscopic lens system which provides a real image of the anterior chamber angle of a patient's eye. One embodiment of the lens system comprises:

(a) a first lens group having a concave posterior surface configured to be placed on a patient's eye;

(b) a second lens group optically aligned with the first lens group; and (c) a stop positioned between the first and second lens groups.

The first and second lens groups may each comprise a plurality of lens elements, and the lens elements may be formed from at least two different types of glass having differing optical properties (e.g., indices of refraction, and/or Abbe number) such that the lens system is achromatic.

Another embodiment of the present invention provides an achromatic gonioscopic lens system which produces a real image of the anterior chamber angle of a patient's eye, comprising:

(a) a first lens group comprising a bi-convex lens subgroup, and a bi-concave contact lens element having a concave posterior surface configured to be placed on a patient's eye, wherein the bi-convex lens subgroup includes at least two materials having different optical properties; and (b) a second lens group optically aligned with the first lens group.

Yet another embodiment of the present invention is an ophthalmoscopy lens system for viewing both the anterior chamber angle and the retina of a patient's eye, comprising:

(a) a first lens group having a concave posterior surface configured to be placed on a patient's eye; and (b) a second lens group optically aligned with the first lens group, wherein the second lens group includes a hole extending through the thickness of the second lens group along the optical axis of the ophthalmoscopy lens system; wherein the ophthalmoscopy lens system may be used to not only provide an image of a patient's anterior chamber angle but also to provide a direct view of a patient's retina through the hole in the second lens system.

BRIEF DESCRIPTION OF THE DRAWINGS

While the specification concludes with claims particularly pointing out and distinctly claiming the present invention, the invention will be further understood from the following detailed description taken in conjunction with the accompanying drawings in which:

DETAILED DESCRIPTION

The present invention provides an ophthalmoscopy lens system which provides a real image of anterior structures within a patient's eye, such as the anterior chamber angle, without the use of reflective surfaces. The lens system is configured to minimize chromatic aberrations and provide improved image contrast, particularly as compared to prior art lens systems (such as those described in U.S. Pat. No. 6,164,779). In addition, one embodiment of the ophthalmoscopy lens system is configured such that, not only may the lens system be used for providing an image of the anterior chamber angle, it may also be used to provide a virtual image of the fundus of a patient's eye (including the retina).

Figure 1:
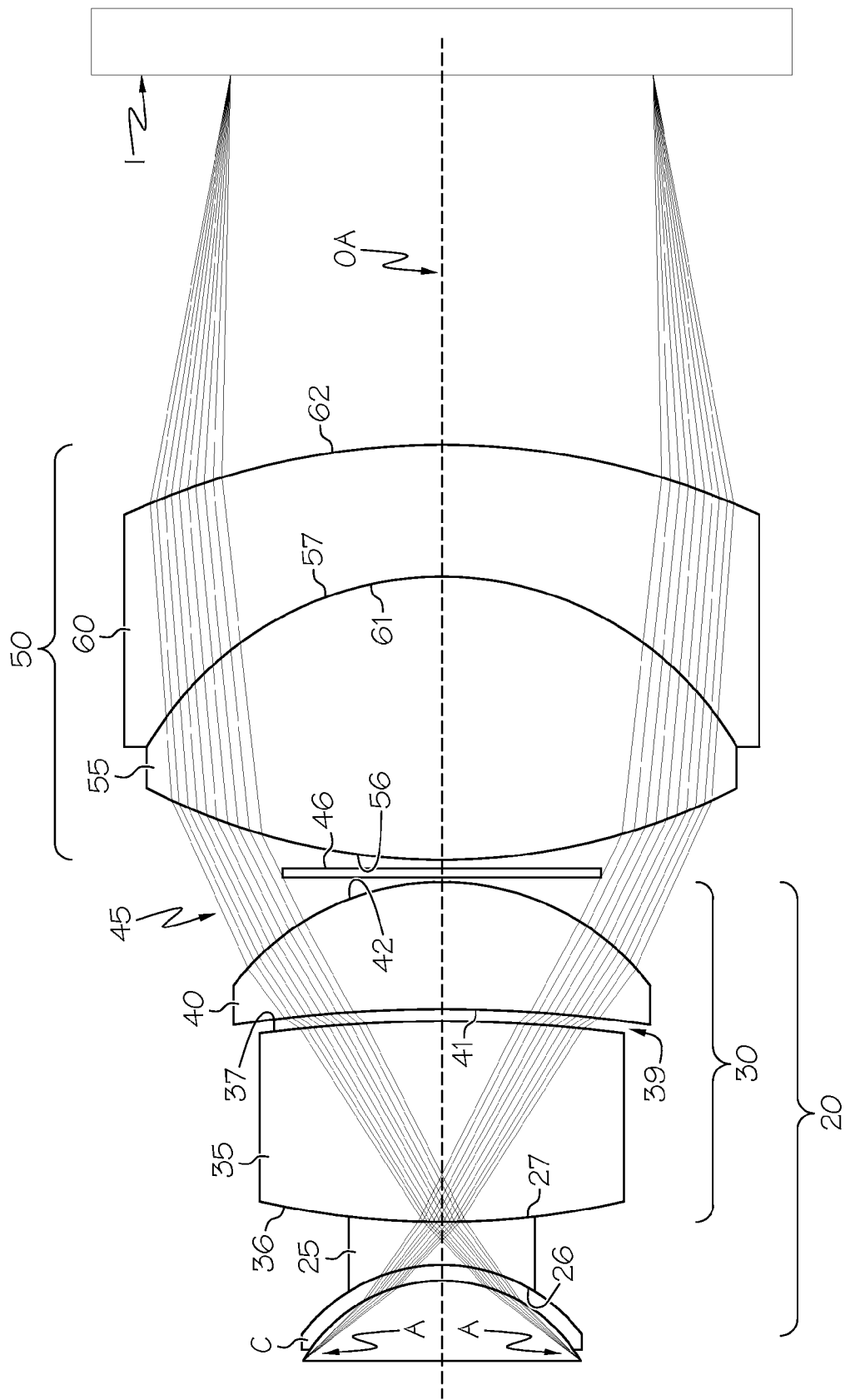
FIG. 1 is a schematic, cross-sectional view of one embodiment of an ophthalmoscopy lens system according to the present invention.

FIG. 1 is a schematic, cross-sectional view of an ophthalmoscopy lens system according to one embodiment of the present invention. The ray tracings in FIG. 1 indicate the path of light rays emanating from the anterior chamber angle A of the eye and passing through the aqueous humor, the cornea C, a tear film, and finally through the lens system of the present invention in order to form an inverted real image of the anterior chamber angle in image plane 1. The tear film is not shown in FIG. 1. During use of the ophthalmoscopy lens system of FIG. 1, a tear film will form between the outer surface of cornea C and concave posterior surface 26 of the lens system. Typically, this tear film will have a thickness of approximately 5–15 μm. For purposes of the ray tracings, the anterior chamber angle is shown as a point source.

In the embodiment of FIG. 1, the ophthalmoscopy lens system comprises a first lens group 20 and a second lens group 50. As used herein, the term "group" is not intended to require the presence of two or more discrete lens elements, unless otherwise indicated. First lens group 20 includes a concave posterior surface 26 configured to be placed upon a patient's eye, specifically upon cornea C. As used herein, the term "posterior surface" refers to the surface of a lens element or lens group which is located nearer to the patient's eye during normal use of the lens system. Concave posterior surface 26 of first lens group 20 is preferably configured so as to substantially correspond to the curvature of an average cornea. During use, any separation between the cornea and concave posterior surface 26 will be filled with a tear layer.

Concave posterior surface 26 of first lens group 20 may have an apical radius of between about 7.5 and about 8.0 mm. In one particular embodiment, the apical radius of surface 26 may be about 7.8 mm, which generally will not require the use of a coupling fluid between the cornea and concave posterior surface 26. Apical radii shorter than about 7.8 mm may require the use of a coupling fluid in order to aid in removal of the lens. Without a coupling fluid, the lens system may develop a suction grip on the eye, making it difficult to remove (although practitioners may desire a suction grip for some procedures).

Concave posterior surface 26 may be provided by a contact lens element 25. In the embodiment shown, contact lens element 25 is biconcave, and concave anterior lens surface 27 of contact lens element 25 has significantly less curvature (i.e., a longer apical radius) than posterior lens surface 26 of contact lens element 25. Contact lens element 25 may be formed from a variety of materials, such as acrylic (particularly polymethylmethacrylate, also referred to as "PMMA"). In fact, one feature of the embodiment shown in FIG. 1 is that posterior lens surface 26 may have an apical radius which is smaller than any other lens surface of the entire lens system.

First lens group 20 not only acts to acts to direct light rays originating at the anterior chamber angle towards second lens group 50 for focusing, first lens group 20 will also at least partially collimate the light rays (as shown in FIG. 1). In this manner, first lens group 20 may be characterized as a collimating lens group, wherein light rays from the anterior chamber angle may be substantially collimated and directed to second lens group 50. In order to provide this collimating feature. first lens group 20 of the embodiment shown in FIG. 1 may also include a bi-convex lens subgroup 30. Bi-convex lens subgroup 30 may comprise one or more individual lens elements, and includes a convex posterior lens surface 36 located adjacent and anterior of contact lens element 25. In the embodiment shown, convex posterior lens surface 36 has the same curvature as anterior lens surface 27 of contact lens element 25, and is cemented thereto using a suitable optical adhesive known to those skilled in the art (such as NOA 61, available from Norland Products, Inc.). Contact lens element 25 and bi-convex lens subgroup 30, as well as the other lens elements described herein, may be coaxially mounted with respect to one another in a frame or other suitable mounting device, as is well-known to those skilled in the art. The frame, however, has been omitted from the drawings for purposes of clarity.

Bi-convex lens subgroup 30 may comprise any number of lens elements (including a single lens element). In the embodiment shown, bi-convex lens subgroup 30 comprises a bi-convex lens element 35 and a meniscus lens element 40. Meniscus lens element 40 is positioned anterior of bi-convex lens element 35. In the embodiment shown in FIG. 1, meniscus lens element 40 is positioned in spaced-apart relationship with respect to bi-convex lens element 35, such that an air space 39 is provided therebetween.

The ophthalmoscopy lens system shown in FIG. 1 is configured to be achromatic. In order to provide such feature, first lens group 20 and/or second lens group 50 may comprise lens elements formed from materials having different optical properties (e.g., indices of refraction and/or Abbe number). As described previously, contact lens element 25 may be formed from a plastic material, such as acrylic (e.g., PMMA). While glass may be used for contact lens element 25, a plastic material will generally be used due to the ease of manufacture and its resistance to chipping. Since the contact lens element will be exposed (i.e., will generally have at least a portion which is not enclosed by the frame), resistance to chipping is significant for the contact lens element. Bi-convex lens element 35 and meniscus lens element 40, on the other hand, are typically formed from glass (either the same or different types of glass). By appropriate selection of the materials used for the various lens elements, the ophthalmoscopy lens system will be achromatic. In one embodiment, contact lens element 25 is plastic (e.g., acrylic), and at least three different glass types are used for the other lens elements.

Second lens group 50 is preferably located in a spaced-apart relationship with respect to first lens group 20, as shown in FIG. 1. In this manner, an air space 45 is provided therebetween. In the embodiment shown in FIG. 1, second lens group 50 is bi-convex, having a convex posterior surface 56 and a convex anterior surface 62.

In the particular example shown in FIG. 1, second lens group 50 comprises a bi-convex lens element 55 located anterior of first lens group 20, and a meniscus lens element 60 positioned anterior of bi-convex lens element 55. Meniscus lens element 60 is cemented to bi-convex lens element 55, as shown. In addition, in the particular configuration shown in FIG. 1, meniscus lens element 60 is configured so as to be slightly negatively-powered. Bi-convex lens element 55 may also be formed from a different material than meniscus lens element 60. In particular, bi-convex lens element 55 may be formed from a material having an index of refraction which is less than that of the material used to form meniscus lens element 60. By way of example, bi-convex lens element 55 may be formed from a glass which would be characterized as a "crown" glass, while meniscus lens element 60 is formed from a glass which would be characterized as a "flint" glass. In this manner, by selection of materials having the appropriate optical properties, such as indices of refraction and/or Abbe numbers, second lens group 50 may comprise an achromatic doublet which provides significant correction of chromatic aberrations (particularly as compared to the lens systems described in U.S. Pat. No. 6,164,779). Second lens group 50 also focuses the light rays in image plane I and will provide the desired magnification. The lens system should also be configured so that the exit ray angle will allow all of the propagated light rays to enter the slit lamp aperture (typically, a 40 mm aperture located 100 mm from the image plane).

The ophthalmoscopy lens system of FIG. 1 is particularly suited for gonioscopy, and therefore may be characterized as a gonioscopic lens system which may be used to provide a real image of the anterior chamber angle A of a patient's eye. Thus, as shown in FIG. 1, this gonioscopic lens system will provide a real image of the anterior chamber angle A, in image plane 1. Although this real image will be inverted, a skilled practitioner is able to use the lens system of FIG. 1 to readily view the anterior chamber angle A.

The lens system of the present invention provides significant improvements over the gonioscopic lens systems described in U.S. Pat. No. 6,164,779 (particularly that shown in FIG. 1 of this prior art patent). The lens systems of the present invention are not only achromatized, they also has improved image contrast. The result is an image superior to that provided by the prior art lens systems. Achromatization is provided by the configuration of the various elements, as described above, as well as the selection of the various materials used to form the individual lens elements.

Image contrast may be further improved by the use of one or more stops. Since the gonioscopic lens system of FIG. 1 is intended for viewing the anterior chamber angle A, light rays emanating from other portions of the patient's eye need not be propagated through the lens system. Such superfluous light rays will reduce image contrast and may otherwise interfere with viewing of the anterior chamber angle. Therefore, it is desirable to eliminate such superfluous and aberrant light rays.

In order to prevent superfluous and aberrant light rays from propagating, the gonioscopic lens system of FIG. 1 may further include one or more stops. For example, a circular or disc-shaped stop 46 may be positioned within air space 45 located between first lens group 20 and second lens group 50. Stop 46 is opaque, and will therefore prevent light rays from propagating through the central region of second lens group 50. If desired, one or more additional stops may be provided in the gonioscopic lens system, such as adjacent convex anterior lens surface 62 of meniscus lens element 60. Once again, a circular or disc-shaped stop member may be used at this location. As yet another alternative, an aperture stop may be positioned between surfaces 27 and 36 in FIG. 1. The stop(s) used in the lens system may be formed from any suitable opaque material, such as plastic (e.g., Delrin).

As an alternative to using a disc-shaped member, portions of one or more lens surfaces may be rendered opaque. By way of example, convex anterior lens surface 42 of meniscus lens element 40 may have a central circular region that is opaque, thereby preventing extraneous light rays from propagating through second lens group 50. This may be accomplished by, for example, simply providing an opaque coating (such as black paint) on convex anterior lens surface 42. Of course, an opaque region may be provided on other lens surfaces in addition to, or in place of, an opaque region on lens surface 42. By proper selection of the size and location of the stop(s), the entrance pupil for the lens system can be controlled. In one embodiment the entrance pupil radius may be between about 0.5 and about 1.5 mm, such as about 1 mm.

It should also be mentioned that, if desired, a flat window or plate may be positioned anterior to meniscus lens element 60 (not shown in FIG. 1). This glass window will act to seal the end of the lens system (when the lens system is mounted in a frame), and may be formed from any suitable material (such as BK7 glass).

Example 1

Although the opthalmoscopy lens system described above can be fabricated in a variety of configurations, applicant has fabricated and tested a specific embodiment of a lens system according to the present invention (and in accordance with the configuration shown in FIG. 1). The prescription for this embodiment of the lens system of FIG. 1 is provided in the tables below (wherein the name of the various glasses is that used by Schott). In the first table, the radius refers to the apical radius of the surface at the point where the surface crosses the optical axis. "CX" denotes a convex surface, and "CV" denotes a concave surface.

| Surface | Material | Radius (mm) | Thickness (mm) | Diameter (mm) | Conic Constant (k) |
|---------|----------|-------------|----------------|---------------|--------------------|
| 26 | Acrylic | 7.81 CV | 2 | 13 | −0.25 |
| 36 | SFL57 | 33.42 CX | 8.7 | 13 | 0 |
| 39 | air space | 58.41 CX | 0.386 | 13 | 0 |
| 41 | LAK8 | 68.745 CV | 5.76 | 18 | 0 |
| 45 | air space | 11.323 CX | 0.837 | 18 | 0 |
| 56 | LAFN28 | 22.026 CX | 12.5 | 25.5 | −3.755 |
| 61 | SFL57 | 14.589 CV | 5.6 | 25.5 | 0 |
| 62 |  | 33.73 CX |  | 27.5 | 0 |

Index of refraction data (at 20° C. and 1.0 atm) for the above surfaces is provided below:

| Surface | Wavelength | | |
|---------|------------|---|---|
|  | 0.470 nm | 0.510 nm | 0.555 nm |
| 26 | 1.49917561 | 1.49606137 | 1.49330470 |
| 36 | 1.87839294 | 1.86453223 | 1.85309358 |
| 39 | 1.0 | 1.0 | 1.0 |
| 41 | 1.72426989 | 1.71954576 | 1.71542223 |
| 45 | 1.0 | 1.0 | 1.0 |
| 56 | 1.78647299 | 1.78086061 | 1.77598724 |
| 61 | 1.87839294 | 1.86453223 | 1.85309358 |
| 62 | 1.0 | 1.0 | 1.0 |

| Surface | 0.610 nm | 0.650 nm |
|---------|----------|----------|
| 26 | 1.49068012 | 1.48915352 |
| 36 | 1.84289659 | 1.83722101 |
| 39 | 1.0 | 1.0 |
| 41 | 1.71154797 | 1.70929379 |
| 45 | 1.0 | 1.0 |
| 56 | 1.77143725 | 1.76880739 |
| 61 | 1.84289659 | 1.83722101 |
| 62 | 1.0 | 1.0 |

A stop positioned within air space 45 (see FIG. 1) may be used to provide an entrance pupil radius of about 1 mm. This may be provided by an opaque disc having a diameter of about 15 mm. If desired, the stop disc may be conically tapered such that the diameter of the face nearest surface 42 is about 13 mm and the diameter of the face nearest surface 56 is about 15 mm (thereby roughly matching the angle of the rays shown in FIG. 1).

A lens system configured in accordance with this example will provide superior image quality as compared to the lens system depicted in FIG. 1 of U.S. Pat. No. 6,164,779.

Figure 2:
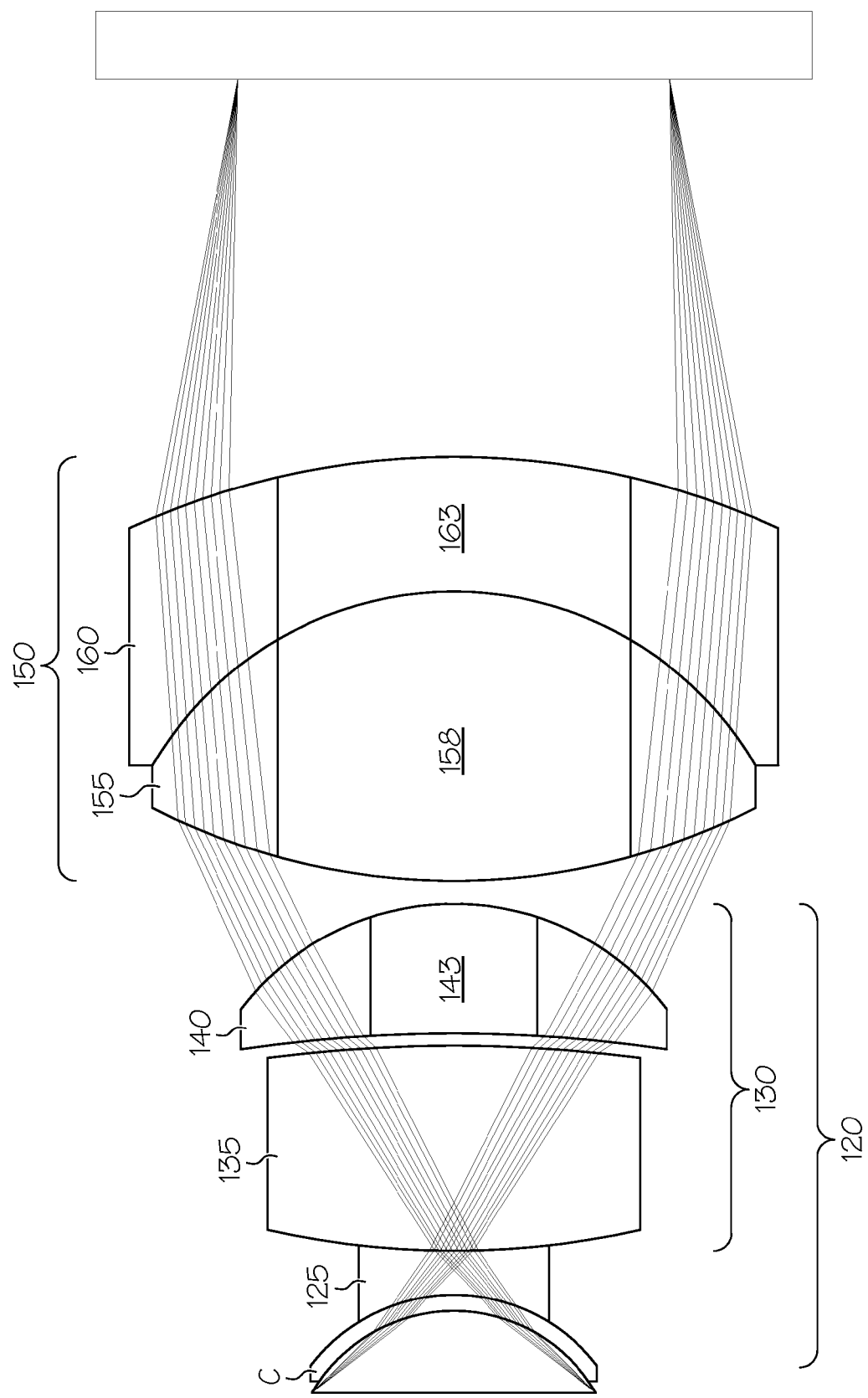
FIG. 2 is a schematic, cross-sectional view of another embodiment of an ophthalmoscopy lens system according to the present invention.

FIG. 2 depicts an alternative embodiment of an ophthalmoscopy lens system according to the present invention. The lens system depicted in FIG. 2 is similar to that shown in FIG. 1, and includes a first lens group 120 and a second, bi-convex lens group 150 arranged in the same manner as described with respect to FIG. 1. First lens group 120 includes a biconcave contact lens element 125, and a bi-convex lens subgroup 130 (comprising a bi-convex lens 135 and meniscus lens 140). Second lens group 150 comprises bi-convex lens 155 and meniscus lens 160. In fact, the above-described lens elements are arranged in the same manner as that described with respect to FIG. 1.

The embodiment of FIG. 2 differs from FIG. 1 in that, instead of one or more stops positioned between the various lens elements, a hole or bore extends along the optical axes of the lens system through the thickness of second lens group 150, and optionally through the thickness of meniscus lens element 140. For example, as shown in FIG. 2, a hole or bore 163 extends axially through the center of meniscus lens 160, and is aligned with a hole or bore 158 which extends axially through the center of bi-convex lens 155. If desired, an axially-extending hole or bore 143 may also extend through the center of meniscus lens 140, as shown, aligned with bores 158 and 163. As seen in FIG. 2, the diameter of bores 158 and 163 may be approximately the same, while the diameter of bore 143 may be smaller (due to the path of light rays through the lens elements). For a lens system constructed in accordance with the Example described above, bores 158 and 163 may have a diameter of about 15 mm, while bore 143 may have a diameter of about 7 mm. In this manner, the entrance pupil radius for the lens system will once again be about 1 mm (since the bores will effectively act as stops).

Since light rays emanating from the anterior chamber angle are not propagated through the central regions of these three lens elements, the holes or bores extending therethrough will not interfere with the formation of a real image of the anterior chamber angle in the manner described previously. However, by providing an axial hole or bore which extends through a portion of the lens system, the ophthalmoscopy lens system of FIG. 2 may also be used for viewing the retina of a patient's eye (as a direct lens system). If desired, a slit lamp or other biomicroscope may be used for this purpose, however, the slit lamp will obviously need to be moved closer to the patient's eye than if used for indirect ophthalmoscopy. The image of the retina will be virtual, however, it will be upright.

In order to scatter stray light rays which propagate through the surface of the bores extending through various lens elements, the surface of bores 143, 158 and 163 may be ground. Alternatively, these surfaces may be rendered opaque. in order to prevent any light rays from propagating through the surface of the bores. For example, the anterior surface of these holes may be painted black in order to prevent the transmission of light therethrough.

We claim:

1. An ophthalmoscopy lens system for viewing both the anterior chamber angle and the retina of a patient's eye, comprising:
   a first lens group having a concave posterior surface configured to be placed on a patient's eye; and
   a second lens group optically aligned with said first lens group, wherein said second lens group includes a hole extending through the thickness of said second lens group along the optical axis of the ophthalmoscopy lens system;
   wherein the ophthalmoscopy lens system may be used to not only provide an image of a patient's anterior chamber angle but also to provide a direct view of a patient's retina through said hole in said second lens group.

2. The ophthalmoscopy lens system of claim 1, wherein the interior walls of said hole are opaque.

3. The ophthalmoscopy lens system of claim 1 wherein said first lens group includes a hole extending from the anterior surface of said first lens group along the optical axis thereof, through a portion of said first lens group.

4. The ophthalmoscopy lens system of claim 1, wherein said first lens group includes a convex anterior surface located adjacent said second lens group.

5. The ophthalmoscopy lens system of claim 4, wherein said second lens group comprises a bi-convex lens group.

6. The ophthalmoscopy lens group of claim 5, wherein said second lens group comprises a bi-convex lens group comprising a doublet component consisting of a bi-convex lens element and a meniscus lens element.

7. The ophthalmoscopy lens system of claim 6, wherein said meniscus lens element is negatively powered, and said bi-convex lens element of said doublet is cemented to said meniscus lens element.

8. The ophthalmoscopy lens system of claim 4, wherein said first and second lens groups are positioned in a spaced-apart relationship.

9. The ophthalmoscopy lens system of claim 8, wherein said first lens group comprises a bi-concave contact lens element and a bi-convex lens subgroup, wherein said bi-convex lens subgroup includes at least two materials having different indices of refraction.

10. The ophthalmoscopy lens system of claim 9, wherein said bi-convex lens subgroup comprises a bi-convex lens element and a meniscus lens element.

11. The ophthalmoscopy lens system of claim 10, wherein said bi-convex lens subgroup comprises a bi-convex lens element and a meniscus lens element positioned in a spaced-apart relationship.

12. An ophthalmoscopy lens system comprising:
   a first lens group comprising a contact lens element having a concave posterior surface configured to be placed on a patient's eye; and
   a second lens group optically aligned with said first lens group, wherein said second lens group includes a hole extending through the thickness of said second lens group along the optical axis of the ophthalmoscopy lens system;
   wherein the ophthalmoscopy lens system is configured to provide not only an image of anterior structures within the patient's eye but also a direct view of a patient's retina through said hole in said second lens group.

13. The ophthalmoscopy lens system of claim 12, wherein said first lens group includes a bi-convex lens subgroup.

14. The ophthalmoscopy lens system of claim 13, wherein said bi-convex lens subgroup comprises a bi-convex lens element and a meniscus lens element positioned anterior of said bi-convex lens element.

15. The ophthalmoscopy lens system of claim 12, wherein said second lens group comprises a bi-convex lens group.

16. The ophthalmoscopy lens system of claim 15, wherein said bi-convex lens group comprises a bi-convex lens element anterior of said first lens group and a meniscus lens element positioned anterior of said bi-convex lens element.

* * * * *